United States Patent [19]

Ohmori et al.

[11] Patent Number: 5,177,776
[45] Date of Patent: Jan. 5, 1993

[54] ONE DIMENSIONAL X-RAY IMAGE SENSOR WITH A CORRECTION FILTER AND X-RAY INSPECTING APPARATUS USING THE SAME

[75] Inventors: Kouichi Ohmori, Toyonaka; Tetsuro Ohtsuchi, Osaka; Hiroshi Tsutsui, Yawata; Sueki Baba, Suita, all of Japan

[73] Assignee: Matsushita Electric Industrial Co., Ltd., Osaka, Japan

[21] Appl. No.: 673,062

[22] Filed: Mar. 22, 1991

[30] Foreign Application Priority Data

Mar. 22, 1990 [JP] Japan .................................. 2-75216

[51] Int. Cl.⁵ ............................................. H05G 1/64
[52] U.S. Cl. ............................................ 378/99; 378/4;
378/54; 378/55; 378/146; 378/156; 378/19;
378/207; 364/413.13; 364/413.14; 364/413.15;
364/413.17
[58] Field of Search .................. 378/99, 4, 54, 55, 56,
378/85, 146, 156, 207, 19; 364/413.13, 413.14,
413.15, 413.17

[56] References Cited

U.S. PATENT DOCUMENTS

| | | |
|---|---|---|
| 3,848,130 | 11/1974 | Macovski . |
| 4,029,963 | 6/1977 | Alvarez et al. . |
| 4,455,669 | 6/1984 | Aichinger et al. .................... 378/97 |
| 4,626,688 | 12/1986 | Barnes ................................. 378/156 |
| 4,811,373 | 3/1989 | Stein ..................................... 378/54 |
| 4,947,414 | 8/1990 | Stein ..................................... 378/55 |
| 4,953,192 | 8/1990 | Plewes ................................. 378/146 |
| 4,980,904 | 12/1990 | Sones et al. ......................... 378/207 |
| 5,033,075 | 6/1991 | DeMone et al. ..................... 378/156 |
| 5,040,199 | 8/1991 | Stein ..................................... 378/56 |

FOREIGN PATENT DOCUMENTS

0168090A1 6/1985 European Pat. Off. .
2477826 1/1981 France .

OTHER PUBLICATIONS

"A Framework for Spectral Artifact Corrections in X-Ray CT", Stonestrom et al., IEEE Transactions on Biomedical Engineering, vol. BME-28, No. 2, Feb., 1981, pp. 128-141.
"A beam-hardening correction using dual-energy computed tomography", Coleman et al., Phys. Med. Biol., 1985, vol. 30, No. 11, 1251-1256, Great Britain.

Primary Examiner—Janice A. Howell
Assistant Examiner—Kim-Kwok Chu
Attorney, Agent, or Firm—Wenderoth, Lind & Ponack

[57] ABSTRACT

A one dimensional X-ray image sensor consists of a plurality of unit detecting devices aligned in a row and a filter which covers a portion thereof and is made of a material having an X-ray absorption coefficient equal to or nearly equal to that of a target material to be inspected. An X-ray inspection apparatus includes the one dimensional X-ray image sensor and further includes a data processor for correcting measured values using data measured in regard to the filter.

9 Claims, 3 Drawing Sheets

ONE DIMENSIONAL X-RAY IMAGE SENSOR WITH A CORRECTION FILTER AND X-RAY INSPECTING APPARATUS USING THE SAME

BACKGROUND OF THE INVENTION

1. Field of the Invention

The present invention relates to a one dimensional X-ray image sensor and an X-ray inspecting apparatus using the same.

2. Description of the Related Art

Recently, there has been noticed an X-ray inspecting apparatus for measuring a content of a target material using X-ray. This utilizes such a phenomenon that the X-ray absorption coefficient of a target material differs in response to the kind of the target material and the energy of X-ray upon irradiating two kinds of X-rays having different energies to an object. For instance, when high energy and low energy X-rays are irradiated to an object comprised of materials A and B, transmissive intensities $I_{l1}$ and $I_{h1}$ of the low energy and high energy X-rays are given as follows.

$$I_{l1} = I_{l0} \exp(-\mu_{la}\rho_a T_a - \mu_{lb}\rho_b T_b) \quad (1)$$

$$I_{h1} = I_{h0} \exp(-\mu_{ha}\rho_a T_a - \mu_{hb}\rho_b T_b) \quad (2)$$

Wherein $I_{l0}$ and $I_{h0}$ are intensities of the low energy and high energy X-rays irradiated. $\mu_{la}$ and $\mu_{ha}$ are mass attenuation coefficients of the material A for the low energy and high energy X-rays, respectively. $\mu_{lb}$ and $\mu_{hb}$ are those of the material B. $\rho_a$ and $\rho_b$ are densities of the materials A and B, respectively, and $T_a$ and $T_b$ are thicknesses of the materials A and B, respectively.

From these two equations (1) and (2), the following equation is introduced.

$$T_b \cdot \rho_b = \{ln(I_{l0}/I_{l1}) \cdot \mu_{ha} - ln(I_{h0}/I_{h1}) \cdot \mu_{la}\}/(\mu_{ha}\mu_{lb} - \mu_{hb}\mu_{la}) \quad (3)$$

From the equation, a product of the thickness $T_b$ and the density $\rho_b$ of the material B, i.e., a content of the material B is obtained by measuring $I_{l1}$ and $I_{h1}$. For instance, the materials A and B may be soft tissue and bone tissue of the human body in bone salt (mineral) analysis, respectively. In this case, an amount of the bone tissue ($T_b \times \rho_b$) is obtained according to the equation (3) by measuring the transmissive intensities $I_{l1}$ and $I_{h1}$ of the low energy and high energy X-rays.

However, so called beam hardening phenomenon is inevitable in such an analysis using X-rays of different energies as mentioned above. This phenomenon is essentially based on an energy distribution of X-ray irradiated from an X-ray source. Absorption of an X-ray having an energy distribution increases as the energy thereof becomes low and the thickness of a target material increases and, accordingly, lower energy components thereof are attenuated much more than higher energy components thereof in transmission through the target material. Due to this, the effective energy of the X-ray after transmission shifts toward higher energy side as compared to that before transmission.

This beam hardening phenomenon gives influences to the mass attenuation coefficients $\mu_{ha}$, $\mu_{hb}$, $\mu_{la}$ and $\mu_{lb}$ since they are dependent on energies of X-ray beams passing through. Thus, the content obtained using the equation (3) is not exact.

SUMMARY OF THE INVENTION

Accordingly, one essential object of the present invention is to provide an X-ray image sensor being free from the beam hardening phenomenon.

Another object of the present invention is to provide an X-ray image sensor having a correction filter made of a material having an X-ray absorption coefficient equal to or near to that of a target material to be inspected.

A further object of the present invention is to provide an X-ray inspection apparatus capable of measuring an exact content of a target material irrespectively to a thickness of a target.

In order to achieve these objects, according to the present invention, there is provided an X-ray image sensor for receiving X-ray beam having been transmitted through an object and outputting electric signals proportional to intensities of the beams received, being characterized by comprising a plurality of unit detecting devices aligned linearly, each unit detecting device outputting an electric signal proportional to an intensity of the beam received and a filter means arranged so as to cover some of said unit detecting devices, said filter means being comprised of a plate-like member having a predetermined thickness which is made of a material having an X-ray absorption coefficient equal to or near to that of a target material to be inspected.

Accordingly to the X-ray image sensor of the present invention, two kinds of data, namely data from the unit detecting devices not covered by the filter means and data from the unit detecting covered thereby are obtained always and a correction coefficient for correcting data obtained can be calculated using the data regarding the filter means.

Accordingly to another aspect of the present invention, there is provided an X-ray inspection apparatus comprising an X-ray generator for generating at least two kinds of X-rays having different effective energies, a multi-channel X-ray image sensor for outputting electric signals proportional to intensities of X-rays received thereby, a filter means arranged so as to cover a part of said multi-channel X-ray image sensor, said filter means having an X-ray absorption coefficient equal to or near to that of a target material to be inspected, a data processing means for calculating a mass content of said target material using outputs from said multi-channel X-ray image sensor, said data processing means further calculating a correction coefficient based on data obtained regarding said filter and said X-ray absorption coefficient, wherein said mass content obtained is corrected by said correction coefficient.

The X-ray inspection apparatus of the present invention is capable of automatically correcting or compensating influences due to so called beam hardening effect of X-ray and fluctuations of the energy of X-ray generated by the X-ray generator.

BRIEF DESCRIPTION OF THE DRAWINGS

These and other objects and features of the present invention will become clear from the following description taken in conjunction with the preferred embodiments thereof with reference to the accompanying drawings throughout which like parts are designated by like reference numerals, and in which.

DETAILED DESCRIPTION OF THE PREFERRED EMBODIMENTS

Figure 1:
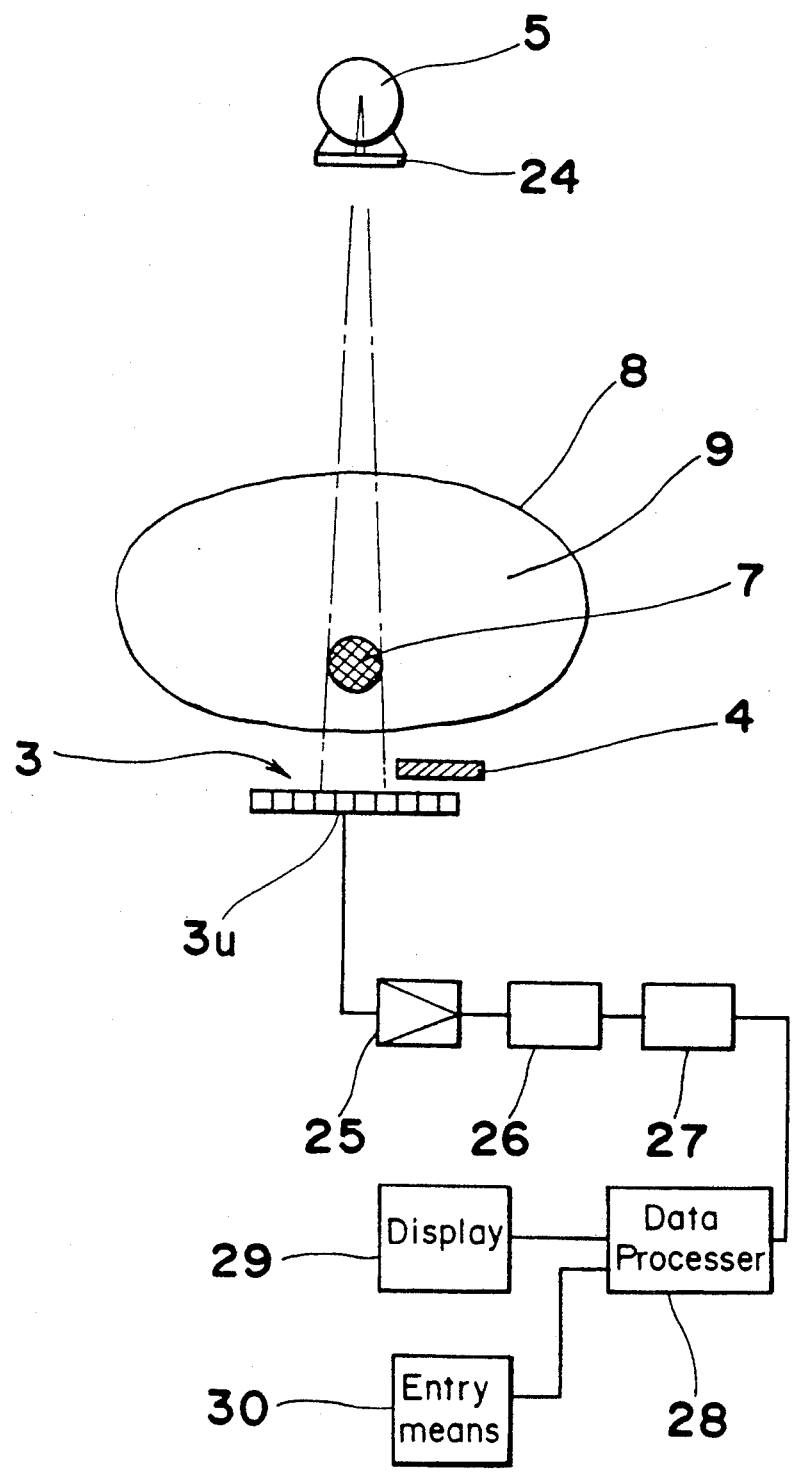
FIG. 1 is a schematical view showing a composition of an X-ray inspection apparatus according to the present invention.

FIG. 1 shows an X-ray inspection apparatus for analyzing the bone salt regarding a bone tissue 7 such as a backbone of a human body 8 comprised of the bone tissue 7 and a soft tissue 9.

Under the human body 8. there is arranged an X-ray image sensor 3 being comprised of a linear array of a plurality of unit detecting devices $3u$ and a plate-like filter 4 arranged so as to cover a portion of the linear array.

Above the human body 8. an X-ray generator 5 such as a cathode ray tube is arranged and irradiates X-ray beams generated, via a K-edge filter 24, to the human body 8. The K-edge filter 24 is made of, for instance, Nd and allows two kinds of X-ray beams splitted to have high and low effective energies to pass therethrough. For instance, when a tube voltage of 80 kV is applied to the X-ray generator 5, X-ray beams having effective energies of 70 keV and 43 keV, respectively, are irradiated to the human body 8 through the K-edge filter 24.

Each unit detection device $3u$ is comprised of a CdTe radiation detector of pulse counting type having a predetermined small detection area. An output therefrom is amplified by a preamplifier 25, is discriminated into signals of high and low levels by a pulse amplitude discriminator 26 and respective numbers of pulses of high and low levels discriminated are counted by a counter circuit 27. Respective count numbers are outputted to a data processor 28 such as a microprocessor and the data processor 28 processes data inputted to obtain the bone salt as will be explained hereinbelow. Results obtained are displayed by a display 29.

Intensities $I_{h0}$ and $I_{l0}$ of the high energy and low energy X-rays to be irradiated are measured beforehand by the image sensor 3 in absence of the human body.

I. Calculation of correction coefficient for correcting influences due to the beam hardening effect Intensities $I_{h1f}$ and $I_{l1f}$ of the high energy and low energy X-rays having passed through the soft tissue 9 and the filter 4 are detected by the unit detection devices $3u$ covered by the filter 4.

The filter 4 is an Al plate of a thickness of 1 cm in the present embodiment. The mass attenuation coefficient of Al is 0.567 cm$^2$/g for 40 keV X-ray and is 0.203 cm$^2$/g for 80 keV X-ray. That of the bone is 0.512 cm$^2$/g for 40 keV X-ray and is 0.209 cm$^2$/g for 80 keV X-ray.

An apparent mass content $(T_f \times \rho_f)$ of the filter 4 is obtained according to the following equation.

$$T_f \cdot \rho_f = \{ln(I_{l0}/I_{l1f}) \cdot \mu_{ha} - ln(I_{h0}/I_{h1f}) \cdot \mu_{la}\}/(\mu_{ha}\mu_{lf} - \mu_{hf}\mu_{la}) \quad (5)$$

wherein $\mu_{la}$ and $\mu_{lf}$: mass attenuation coefficients of the soft tissue and the filter for the low energy X-ray, respectively.

$\mu_{ha}$ and $\mu_{hf}$: mass attenuation coefficients of the soft tissue and the filter for the high energy X-ray, respectively.

$\rho_a$ and $\rho_f$: densities of the soft tissue and the filter, respectively.

$T_a$ and $T_f$: thicknesses of the soft tissue and the filter, respectively.

The mass content of the filter 4 obtained is shifted from the true value by the beam hardening effect, as stated above. Since the density and the thickness of the filter 4 is known beforehand, the true value of the mass content of the filter 4 is easily obtained from these.

Accordingly, the correction coefficient $K_1$ for compensating the beam hardening effect is obtained as follows $$K_1 = T_f \times \rho_f(\text{true value})/T_f \times \rho_f(\text{measured value}) \quad (6)$$

II. Calculation of Bone salt

Intensities $I_{h1b}$ and $I_{l1b}$ of the high energy and the low energy X-rays having passed through the soft tissue 9 and the bone tissue 7 are also detected by the unit detecting devices $3u$ uncovered by the filter 4. An apparent mass content of the bone 7 i.e. bone salt is obtained according to the equation (3) by equating $I_{l1}$ and $I_{h1}$ to $I_{lb}$ and $I_{h1b}$, respectively.

Namely, $$T_b \cdot \rho_b = \{ln(I_{l0}/I_{l1b}) \cdot \mu_{ha} - ln(I_{h0}/I_{h1b}) \cdot \mu_{la}\}/(\mu_{ha}\mu_{lb} - \mu_{hb}\mu_{la}) \quad (3')$$

Since the mass content of the filter 4 is chosen so that it is nearly equal to that of the bone tissue 9, the most probable value of the bone salt is obtained by correcting the measured value with the correction coefficient $K_1$ calculated beforehand. Namely, it is obtained as follows.

$$T_b \times \rho_b(\text{most probable}) = K_1 \times T_b \cdot \rho_b(\text{measured}) \quad (7)$$

III. Sensitivity correction for each unit detecting device

Prior to the measurement of the bone salt, the X-ray to be irradiated is detected by all the unit detecting devices of the X-ray image sensor without the human body and in a state that the filter is removed. The sensitivity of each unit detecting device $3u$ can be corrected from a shift amount of a measured count number thereof from a mean value obtained by averaging all measured count numbers.

Respective correction coefficients thus obtained are inputted from a data entry section 30 such as a key board to the data processor 28 beforehand.

Count numbers outputted from respective unit detecting devices are corrected using these correction coefficients, respectively, and thereby, the accuracy of measurement is highly improved.

Though an Al plate is used for the filter 4 in the above embodiment, materials equivalent to the bone tissue such as calcium carbonate, kalium hydrogenphosphate, potassium iodide and the like are available therefor.

Further, the unit detecting device is not limited to the CdTe radiation detector and semiconductor radiation detectors made of Si, Ge, GaAs and the like, scintillation detector, ion chamber detector and the like are available therefor.

Also, various known ways to generate X-rays having different energies are available other than the K-edge filtering method.

Figure 2:
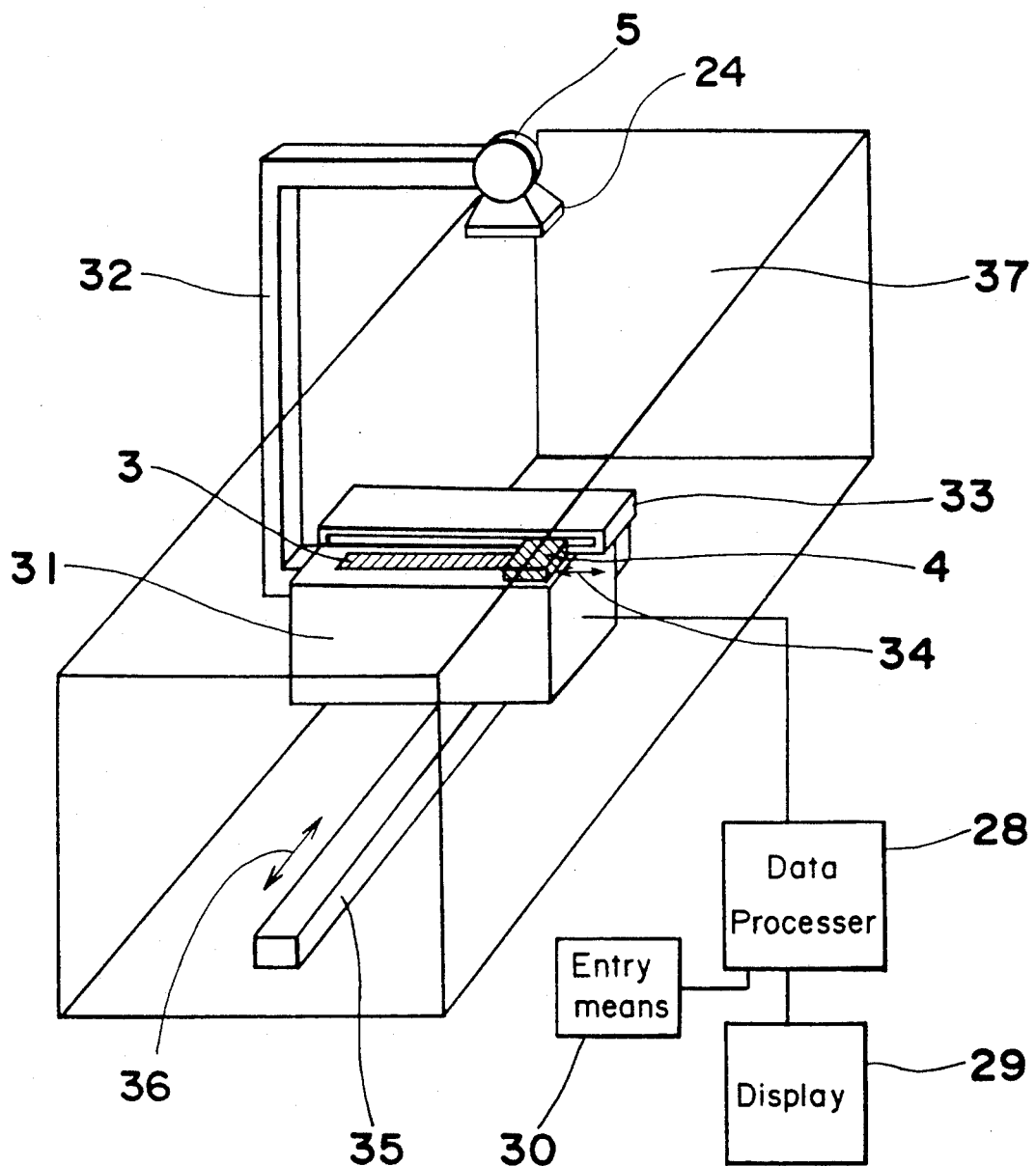
FIG. 2 is a schematical perspective view of the X-ray inspection apparatus installed to a bed.
Figure 3:
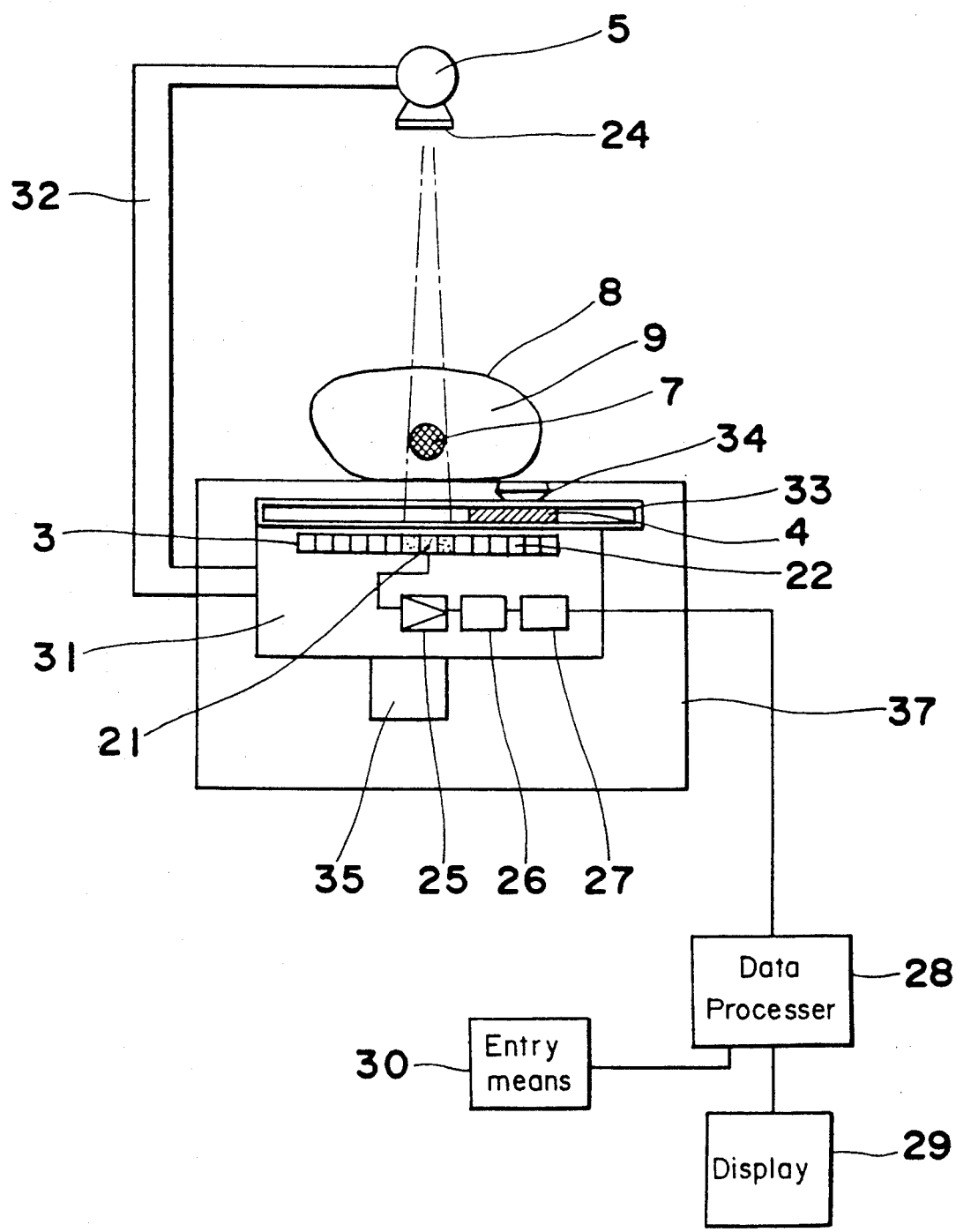
FIG. 3 is a cross-sectional view of FIG. 2.

FIG. 2 shows an example of the bone salt analyzing system.

A carrier box 31 is arranged under a bed 37 which is movable in a lengthwise direction of the bed 37 and is driven by a driving means 35. Though a concrete composition of the driving means 35 is not shown in FIG. 2, a suitable known mechanism such as a linear motor can be employed to drive the carrier box 31.

The carrier box 31 provides an X-ray image sensor 3 on the upper surface thereof which is arranged in a direction of the width of the bed and carries a driving means 33 for moving a filter 4 along the X-ray image sensor 3.

Above the bed 37, an X-ray generator 5 is supported by an arm 32 fixed to the carrier box 31 so that the X-ray generator 5 is moved together with the X-ray image sensor 3. The X-ray generator 5 provides with a K-edge filter 24 for generating high and low energy X-rays.

Prior to a measurement of the above salt, the filter 4 is moved to a position whereat all unit detecting devices are uncovered thereby to detect the sensitivity of each unit detecting device. By irradiating the high and low energy X-rays to the X-ray image sensor 3 in absence of a human body, each of outputs from the unit detecting devices is read out as a count number. Assuming that $I_{li}$ and $I_{hi}$ are count numbers of i-th unit detecting device for the low and high energy X-rays and $I_{l\ av}$ and $I_{h\ av}$ mean values averaged over all count numbers $I_{li}$ and $I_{hi}$, respectively, respective correction factors $K_{2li}$ and $K_{2hi}$ of i-th unit detecting device for the low and high energy X-rays are given as follows.

$$K_{2li} = I_{li}/I_{l\ av} \quad (8)$$

$$K_{2hi} = I_{hi}/I_{h\ av} \quad (9)$$

Sensitivities of respective unit detecting devices are corrected using correction factors obtained according to the equations (8) and (9), namely, an output of i-th unit detecting device is corrected using $K_{2li}$ and $K_{2hi}$ by the data processor 28. Calculation of the mean values and correction factors is done in the data processor 28 and data obtained by the calculation are stored therein to correct outputs from individual unit detecting devices upon measuring the bone salt.

Upon starting the measurement, a human body is set on the bed 37 and the filter 4 is moved to cover some of the unit detecting devices lying under a part of the human body including only the soft tissue thereof. Thereafter, the X-ray generator 5 is energized to generate the high and low energy X-rays and the X-ray image sensor 3 receives X-rays passing through the human body 8.

The most probable value of the bone salt is calculated by the data processor 28 according to the method as explained regarding FIG. 1. To measure the bone salt along a length of the bone, the X-ray image sensor 3 and the X-ray generator 5 is scanned in the lengthwise direction of the bed 37 by driving the carrier box 31 by the driving means 35 therefor.

It is to be noted that a time-dependent fluctuation of the intensity of X-ray is also compensated by the present invention since the correction coefficient $K_1$ obtained using the filter 4 upon every measurement includes influences due to the time-dependent fluctuation.

Thus, the bone salt obtained finally is free from the beam hardening effect, deviations of the sensitivity of each unit detecting device and the time-dependent fluctuation of the intensity of X-ray and, accordingly, represents the real value exactly.

In the preferred embodiment, the present invention is applied to the bone salt analysis but is not limited to this and, for instance, is applicable for measuring a content of Cu contained in a plastic material. In this case, the material for the filter is Cu.

Although the present invention has been fully described in connection with the preferred embodiments thereof with reference to the accompanying drawings, it is to be noted that various changes and modifications are apparent to those skilled in the art. Such changes and modifications are to be understood as included within the scope of the present invention as defined by the appended claims unless they depart therefrom.

What is claimed is:

1. A multi-channel X-ray image sensor for receiving X-ray beams having been transmitted through a target including an element therein, said element being made of a material having an X-ray absorption coefficient different from that of the material forming the remaining portion of said target, and for outputting electrical signals proportional to intensities of the beams received, said sensor comprising:
   a plurality of unit X-ray image sensors arranged so as to form a multi-channel X-ray image sensor, each of said unit X-ray image sensors outputting an electrical signal proportional to an intensity of the beam received thereby; and
   a filter means disposed between the transmitted X-ray beams and said unit X-ray image sensors comprised of a plate-like member having a predetermined thickness which is made of a material having an X-ray absorption coefficient equal to or near to that of said element included in said target;
   wherein said filter means is arranged in such a manner that it cover only unit X-ray image sensors which receive beams which have only been transmitted through a part of said remaining portion of said target.

2. The X-ray image sensor as claimed in claim 1, wherein said filter means is movable along the lengthwise direction of said X-ray image sensor.

3. The X-ray image sensor as claimed in claim 2, wherein said filter means is made of a material having an X-ray absorption coefficient equal to or near to that of a biological bone tissue.

4. The X-ray image sensor as claimed in claim 1, wherein said filter means is made of a material having an X-ray absorption coefficient equal to or near to that or a biological bone tissue.

5. An X-ray inspection apparatus for inspecting a biological target comprised of a soft tissue and a bone tissue, said apparatus comprising:
   an X-ray generator for generating at least two kinds of X-rays having different energies;
   a multi-channel X-ray image sensor for outputting electrical signals proportional to intensities of X-ray beams received by each channel thereof;
   a filter means disposed between said X-ray generator and said multi-channel X-ray image sensor, comprised of a plate-like member having a predetermined thickness which is made of a material having an X-ray absorption coefficient equal to or near to that of said bone tissue, said filter means being arranged so as to cover only channel which receive beams which have only been transmitted through a part of said soft tissue; and a data processing means for calculating a mass content of said bone tissue using information obtained simultaneously by said multi-channel X-ray image sensor, said information being obtained from beams having been transmitted through said soft tissue only, said soft tissue and bone tissue, and said soft tissue and said filter means, respectively.

6. The X-ray inspection apparatus as claimed in claim 5, wherein said filter means is movable relatively to said multi-channel X-ray image sensor.

7. The X-ray inspection apparatus as claimed in claim 5, wherein said X-ray generator and said X-ray image sensor are supported so as to oppose to each other by a carrier and said carrier is movable at least in one direction.

8. The X-ray inspection apparatus as claimed in claim 6, wherein said filter means is moved so as not to cover any portion of said multi-channel X-ray image sensor prior to an inspection measurement of said target material an, thereby data regarding sensitivities of individual channels of said multi-channel X-ray image sensor are obtained.

9. The X-ray inspection apparatus as claimed in claim 6, wherein said X-ray generator and said X-ray image sensor are supported so as to oppose to each other by a carrier and said carrier is movable at least in one direction.

* * * * *